United States Patent [19]
Yada et al.

[11] Patent Number: 5,624,839
[45] Date of Patent: Apr. 29, 1997

[54] PROCESS FOR CULTURING HEPATOCYTES FOR FORMATION OF SPHEROIDS

[75] Inventors: Toshikazu Yada, Nagoya; Norio Koide, Okayama; Koji Kimata, Nagoya, all of Japan

[73] Assignee: Seikagaku Kogyo Kabushiki Kaisha (Seikagaku Corporation), Tokyo, Japan

[21] Appl. No.: 453,932

[22] Filed: May 30, 1995

Related U.S. Application Data

[62] Division of Ser. No. 312,676, Sep. 28, 1994, abandoned, which is a continuation of Ser. No. 937,290, Aug. 31, 1992, abandoned.

[30] Foreign Application Priority Data

Aug. 30, 1991 [JP] Japan .................... 3-244152

[51] Int. Cl.$^6$ .................... C12N 5/00; A61K 31/715; C07H 1/00
[52] U.S. Cl. .................... 435/378; 435/402; 435/395; 514/54; 514/56; 536/21; 536/53; 536/54; 536/55; 536/55.1; 536/124; 536/123.1
[58] Field of Search .................... 514/54, 56; 536/21, 536/53, 54, 55, 55.1, 124, 123.1; 435/240.2, 240.21, 240.243

[56] References Cited

U.S. PATENT DOCUMENTS

| | | | |
|---|---|---|---|
| 4,239,754 | 12/1980 | Sache et al. | 514/56 |
| 4,352,883 | 10/1982 | Lin | 435/178 |
| 4,352,887 | 10/1982 | Reid et al. | 435/240 |
| 4,385,046 | 5/1983 | Milbrath et al. | 536/21 |
| 4,391,909 | 7/1983 | Lim | 435/178 |
| 4,745,105 | 5/1988 | Griffin et al. | 514/56 |
| 4,755,379 | 7/1988 | Jozefonvicz et al. | 514/56 |
| 4,859,581 | 8/1989 | Nicolson et al. | 435/7.4 |
| 4,942,129 | 7/1990 | Goosen et al. | 435/182 |
| 4,956,128 | 9/1990 | Hommel et al. | 264/4 |
| 4,997,819 | 3/1991 | Yamaguchi et al. | 514/54 |
| 5,270,192 | 12/1993 | Li et al. | 435/174 |

FOREIGN PATENT DOCUMENTS

| | | |
|---|---|---|
| 4169530 | 4/1991 | Japan . |
| WO92/01720 | 2/1992 | WIPO . |

OTHER PUBLICATIONS

R.T. Morrison and R.N. Boyd *Organic Chemistry*, 4th Ed. Allyn and Bacon, Inc., Boston, 1983, p. 891.
Kjellen et al; PNAS (USA) 78(9):5371–5375 1981.
Kim et al; Thrombosis Research 56:369–376 (1989).
Hall et al; Biomaterials 10(4):219–224 (1989).
Denkinger et al; Chemical Abstracts 113:134655c (1990).
Soeda et al; Biochemistry 29(21):5188–5194 (May 1990).
Database WPI, Section Ch, Week 8950, Nov. 7, 1989.
Biological Abstracts, vol. 88, Abstract No. 029387, 1988.
J. Clin. Electron Microscopy, 22(2), pp. 243–252 (1989).
Jpn. J. Artif. Organs, 20(1), pp. 139–144 (1991).
Acta. Hepatologica. Japonica, 29(11), pp. 1547–1549 (1988).
Kan. Tan. Sui., 20(4), pp. 585–591 (1990).
Cell, 22(5), pp. 167–172 (1990).
Olympus Microscope Review, 17, pp. 30–33 (1990).
Artif. Organs, 15(6), pp. 474–480 (1991) (Abstract).
Exp. Cell Res., 186, pp. 227–235 (1990).
Cell Struct. Funct., 13, pp. 179–188 (1988).
Biochem. Biophys. Res. Commun., 161(1), pp. 385–391 (1989).
Jpn. J. Artif. Organs, 20(1), pp. 150–155 (1991).
Journal of Japan Surgical Society, 92(9), pp. 1272–1275 (1991).

*Primary Examiner*—Gary L. Kunz
*Assistant Examiner*—Kathleen Kahler Fonda
*Attorney, Agent, or Firm*—Sughrue, Mion, Zinn, Macpeak & Seas

[57] ABSTRACT

Hepatocytes spheroids can be formed by culturing hepatocytes in a culture vessel using a lipid-bound glycosaminoglycan as a culture substrate. Floating spheroids of hepatocytes can be obtained efficiently, which are capable of maintaining liver-specific functions and of keeping the spheroid form stably for a prolonged period of time.

3 Claims, 2 Drawing Sheets

 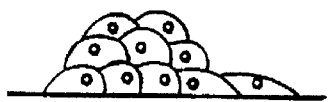 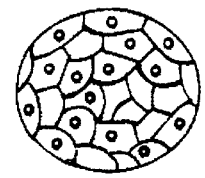
FIG.1A   FIG.1B   FIG.1C
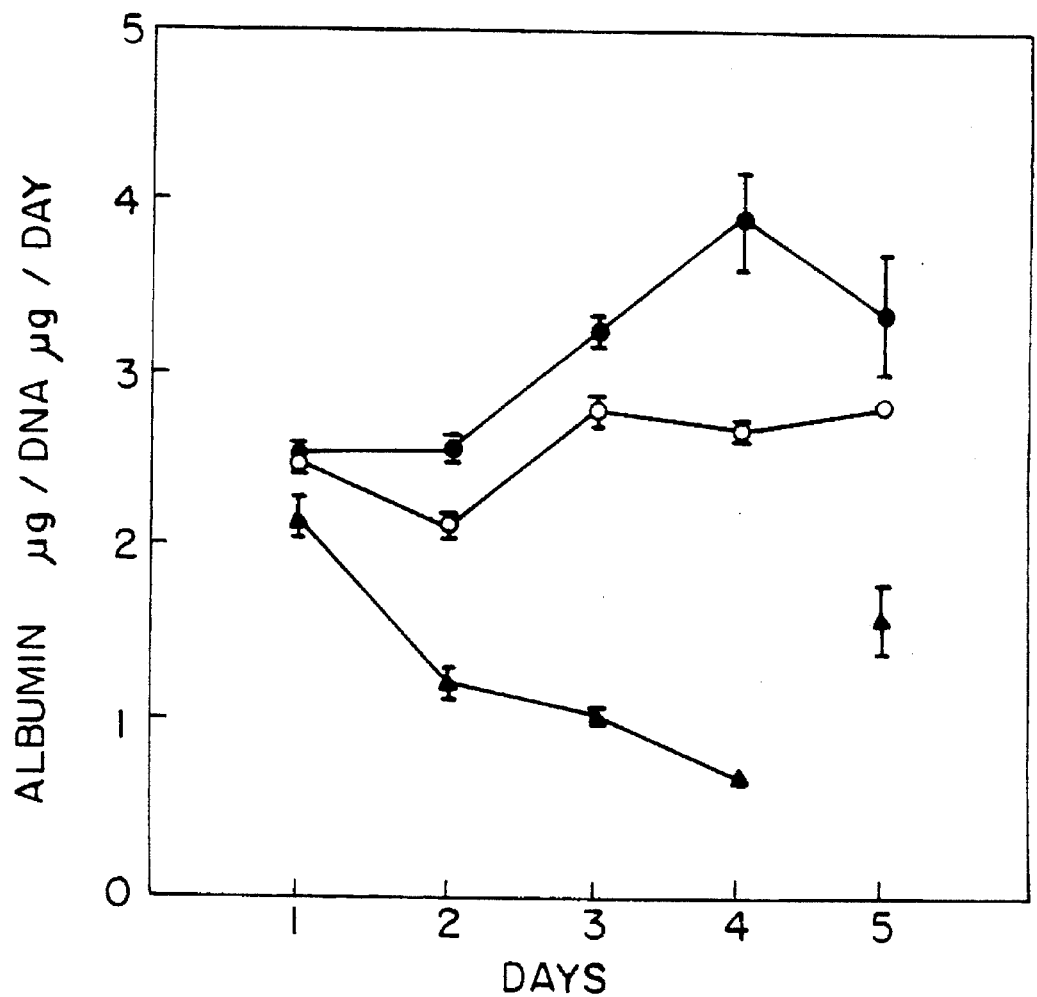
FIG.3

PROCESS FOR CULTURING HEPATOCYTES FOR FORMATION OF SPHEROIDS

This is a Divisional of application Ser. No. 08/312/676 filed on Sep. 28, 1994,(abandoned), which is a Continuation of application Ser. No. 07/937,290 filed Aug. 31, 1992 (abandoned).

FIELD OF THE INVENTION

The present invention relates to an agent effective for forming hepatocyte spheroids that functions as an artificial liver function aid, which comprises a covalently lipid-bound glycosaminoglycan, and to a process for formation of the spheroids which comprises culturing hepatocytes in a vessel in the presence of the agent as a culture substrate.

BACKGROUND OF THE INVENTION

The liver is an important organ in an animal which takes part in the metabolism, and the liver function is originated from hepatocytes that occupies about 70% of the liver. Such a function is effected not simply by the hepatocytes but by their interactions with non-parenchymal cells and extracellular matrix, and by the construction of tissue based on these interactions. In other words, biological activities of the liver in the living body are effected by the formation of spheroids in which hepatocytes are adhered to one another.

Previously, the inventors of the present invention have conducted studies on the method of culturing hepatocytes for formation of spheroids with retaining their functions, and discovered a substance related to the reconstitution of tissue morphology of hepatocytes capable of maintaining the liver function at a high level. Based on this finding, the inventors have also succeeded in forming spheroids of hepatocytes which can express and maintain their functions at high levels for a prolonged period of time, by culturing hepatocytes in the presence of the above-described substance, and in reproducing the tissue construction to a certain degree.

That is, as shown in FIG. 1, when hepatocytes were isolated from adult rat livers by a collagenase-liver-perfusion method, inoculated in a culture dish which has been coated with proteoglycan(s) of liver reticulin fibers and then cultured statically in serum-free hormone-defined medium (HDM) supplemented with the necessary hormones such as EGF (epidermal growth factor), insulin and the like, the inoculated hepatocytes attached to the coated substrate to form monolayers during the initial stage of the cultivation, and, as the cultivation progressed, the monolayers assembled to form multilayer islands and the multilayer islands shrunk to form spherical cell clusters which subsequently separated from the surface of the dish to form floating spheroids in the liquid medium (Cell Struct. Funct., 13, 179 (1988), Biochem. Biophys. Res. Commun., 161, 385 (1989)).

It has been revealed that the glycan moiety of the above-described reticulin-originated proteoglycan(s) consisted of dermatan sulfate, heparan sulfate and other unknown sugars. However, when culture dishes were coated with chondroitin sulfate, dermatan sulfate, heparan sulfate or an adhesive substrate such as collagen extracted from rat livers or fibronectin fractions or a glycoprotein, hepatocytes spread in the dishes but remained in the state of monolayers and did not form spheroids.

When hepatocytes are cultured in a positively charged polystyrene plastic dish, they form floating spheroids similar to the case of their cultivation in a proteoglycan-coated culture dish. It is considered that such a phenomenon occurs because hepatocytes secrete proteoglycan(s) when inoculated in this type of plastic dish and the secreted proteoglycan(s) adhere to the surface of the dish (Exp. Cell Res., 186, 227 (1990), JP-A-1-277486 (the term "JP-A" used herein means an "unexamined published Japanese patent application")).

When cultured in the presence of the proteoglycan as a culture substrate, hepatocytes form floating spheroids which are stable even after a relatively prolonged cultivation period. It has been reported that the hepatocyte spheroids could maintain liver-specific differentiation function at a high level, because they were able to secrete albumin at a high level constantly for a prolonged period of time in comparison with monolayers of hepatocytes, and that the hepatocyte spheroids possibly showed a tissue reconstruction quite close to the in vivo structure, because they hardly showed activity in cell proliferation at least when checked by $^3$H-thymidine incorporation and nuclear labeling index (J. Clin. Electron Microscopy, 21, 5 (1988)).

However, since the proteoglycan(s) cannot be easily prepared from reticulin fibers in high yield, great concern has been directed toward the deveopment of a culture substrate which, as a substitute of the proteoglycan(s), can induce spheroids formation of hepatocytes efficiently and is effective for the continuative expression of hepatocyte differentiation functions. In addition, it is required to culture hepatocytes in vitro for a prolonged period of time with retaining their in vivo functions for development of a biological artificial liver function-aiding device.

SUMMARY OF THE INVENTION

An object of the present invention is to provide an agent for forming hepatocyte spheroids, which comprises a covalently lipid-bound glycosaminoglycan. Effects of the agent of the present invention to induce spheroids and to express and maintain hepatocyte differentiation functions are markedly superior to those of the proteoglycans originated from reticulin fibers.

The present invention also provides a process for culturing hepatocytes for formation of the spheroids which comprises culturing hepatocytes in the presence of the agent as a culture substrate and the hepatocyte spheroids thus prepared.

BRIEF DESCRIPTION OF THE DRAWINGS

FIG. 1 depicts three assembling modes of hepatocytes, in which A, B and C show monolayers, multilayer island-like hemispheroids and spheroids, respectively.

FIG. 3 is a graph showing secretory albumin production ability of hepatocyte spheroids obtained by using culture dishes coated with CS-PPEADP and the like, in which -●- is a line for CS-PPEADP-coated dish, -○- for uncoated positively charged polystyrene plastic dish and -▲- for collagen-coated dish.

DETAILED DESCRIPTION OF THE INVENTION

Figure 2:
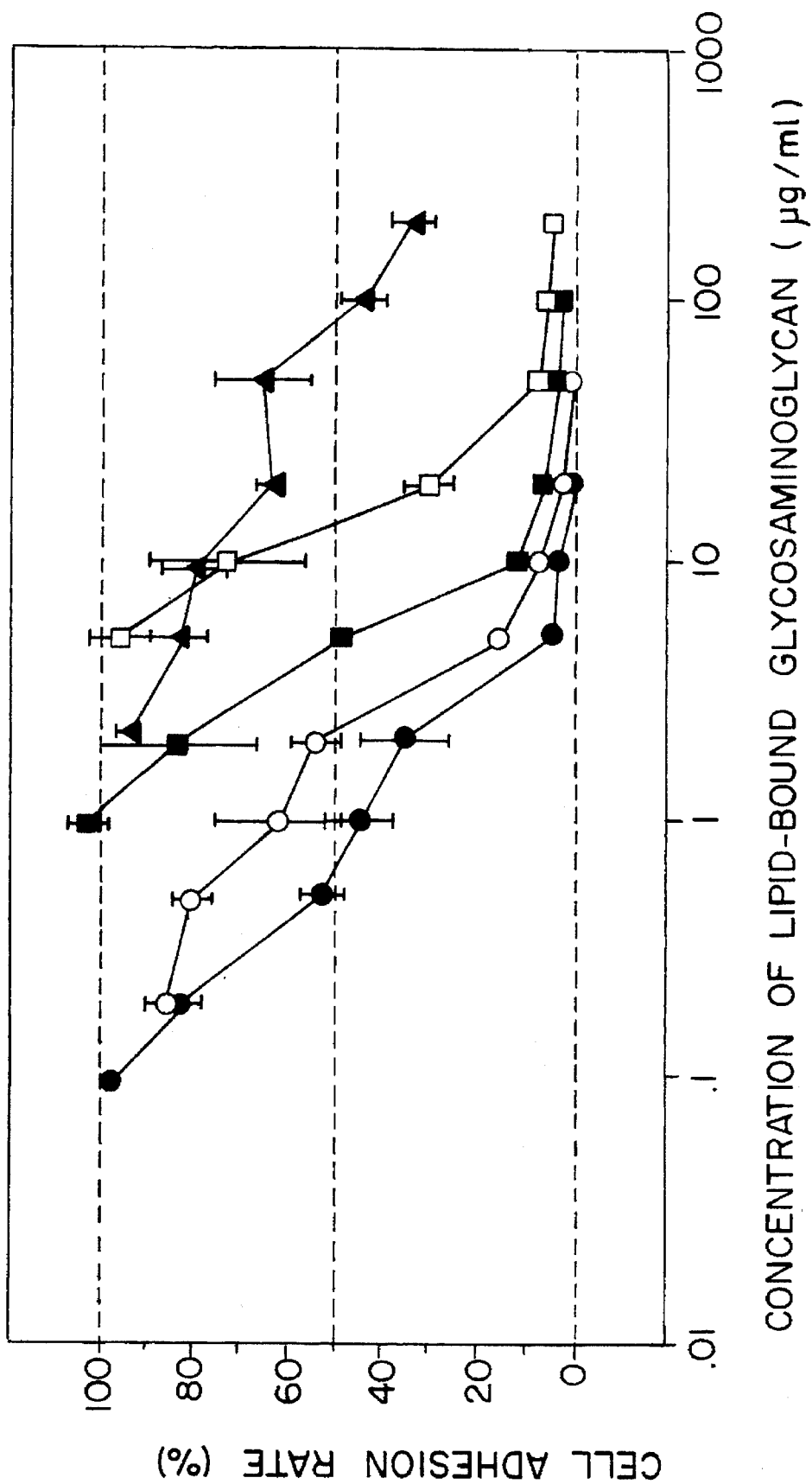
FIG. 2 is a graph showing adhesion rate of BHK-21 cells to culture dishes coated with fibronectin and various phospholipid-bound glycosaminoglycans, in which -●- is a line for CS-PPEADP-coated dish, -○- for DS-PPEADP-coated dish, -▲- for CH-PPEADP-coated dish, -□- for HA-PPEADP-coated dish and -■- for HS-PPEADP-coated dish.

The hepatocyte spheroids forming agent of the present invention comprises a glycosaminoglycan (referred to as "GAG" in some cases hereinafter) to which a lipid is covalently bound. Preferably, a covalent bond between a lipid and a GAG includes a CONH bond, an ester bond or a CH$_2$NH bond formed between a carboxyl group including lactone, a formyl group, a hydroxyl group or primary amino group of a GAG and a primary amino group, a carboxyl group or a formyl group of a lipid. Particularly preferred covalent bonds are (1) a CONH bond between a carboxyl group including lactone of a glycosaminoglycan whose reducing terminal is cleaved and a primary amino group of a lipid, (2) a CONH bond between a carboxyl group of a uronic acid moiety of a glycosaminoglycan and a primary amino group of a lipid or (3) a CH$_2$NH bond between a formyl group of a glycosaminoglycan whose reducing terminal is cleaved and a primary amino group of a lipid.

A primary amino group, a carboxyl group, a formyl group or a hydroxyl group which takes part in the above bond may be inherently contained in a GAG or a lipid, or may be formed by a chemical treatment of the GAG or lipid or introduced in advance into the GAG or lipid through a reaction with a spacer compound which has the above functional group as its terminal groups.

The following shows typical examples of the relationship between the lipid-bound GAG and its material compounds.

(1) GAG or derivatives thereof

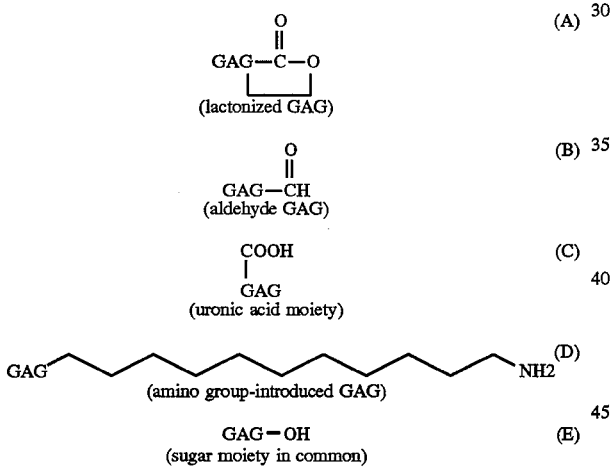

In the above formula, GAG is a glycosaminoglycan and ⋯NH$_2$ represents an introduced amino group.

(2) Lipid or derivatives thereof (i) lipid-NH$_2$
  (amino group-containing phospholipid)
  (ii) lipid ⋯NH$_2$
  (amino group-introduced lipid)
  (iii) lipid ⋯COOH
  (carboxyl group-introduced lipid)

$$\overset{O}{\underset{\|}{\text{(iv) lipid-CH}}} \quad \text{(aldehyde lipid)}$$

In the above formulae, ⋯COOH represents an introduced carboxyl group.

Throughout the specification, variables within the same formula have the same definition.

(3) Lipid-bound GAG

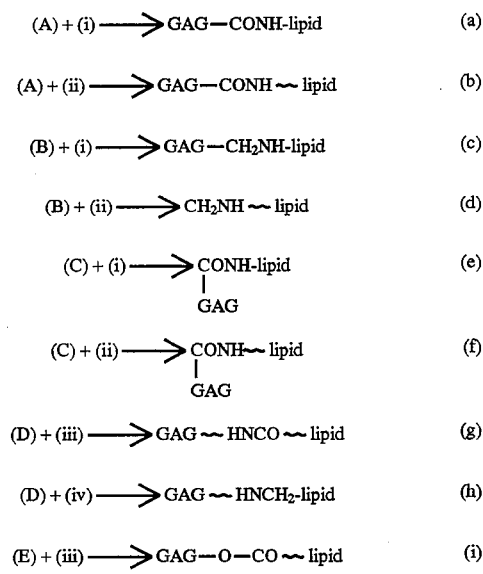

The lipid-bound glycosaminoglycan of the present invention can be used as a salt, preferably with an alkali metal such as sodium and potassium, an alkaline earth metal such as calcium and magnesium, an amine such as trialkylamine, and an organic base such as pyridine.

The following are examples of the lipid-bound glycosaminoglycans of the present invention.

1. A lipid-bound glycosaminoglycan represented by the following formula:

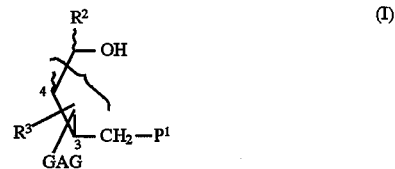

wherein P$^1$ is a lipid having a primary amino group, GAG is a glycosaminoglycan residue and;

(1) GAG is located at the 4-position, R$^3$ is located at the 3-position, R$^2$ is a COOH group and R$^3$ is an OH group when GAG is a glycosaminoglycan residue of hyaluronic acid, chondroitin, chondroitin sulfate A, C or E, dermatan sulfate, heparin or heparan sulfate excluding a reducing terminal glucuronic acid moiety or when GAG is a glycosaminoglycan residue of dermatan sulfate excluding a reducing terminal iduronic acid moiety, (2) GAG is located at the 4-position, R$^3$ is located at the 3-position, R$^2$ is a COOH group and R$^3$ is an OSO$_3$H group when GAG is a glycosaminoglycan residue of chondroitin sulfate K or chondroitin polysulfate excluding a reducing terminal glucuronic acid moiety, (3) GAG is located at the 3-position, R$^3$ is located at the 4-position, R$^2$ is a CH$_2$OH group and R$^3$ is an OH group when GAG is a glycosaminoglycan residue of keratan sulfate excluding a reducing terminal galactose moiety, and (4) GAG is located at the 3-position, R$^3$ is located at the 4-position, R$^2$ is a CH$_2$OSO$_3$H group and R$^3$ is an OH group when GAG is a glycosaminoglycan residue of keratan polysulfate excluding a reducing terminal galactose moiety.

2. A lipid-bound glycosaminoglycan represented by the following formula:

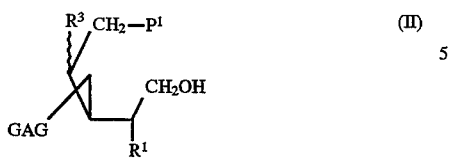

wherein $P^1$ is a lipid having a primary amino group, GAG is a glycosaminoglycan residue and;
  (1) $R^1$ is a $NHCOCH_3$ group and $R^3$ is an OH group when GAG is a glycosaminoglycan residue of hyaluronic acid or chondroitin excluding a reducing terminal hexosamine moiety,
  (2) $R^1$ is a $NHCOCH_3$ group and $R^3$ is an OH group when GAG is a glycosaminoglycan residue of chondroitin sulfate A or K, chondroitin polysulfate or dermatan sulfate excluding a reducing terminal hexosamine moiety, and
  (3) each of $R^1$ and $R^3$ is an OH group when GAG is a glycosaminoglycan residue of keratan sulfate or keratan polysulfate excluding a reducing terminal galactose moiety.

3. A lipid-bound glycosaminoglycan represented by the following formula:

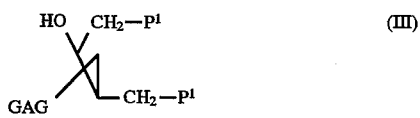

wherein $P^1$ is a lipid having a primary amino group and GAG is a glycosaminoglycan residue of keratan sulfate or keratan polysulfate excluding a reducing terminal galactose moiety.

4. A lipid-bound glycosaminoglycan represented by the following formula:

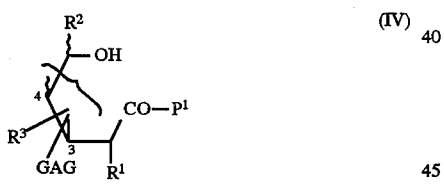

wherein $P^1$ is a lipid having a primary amino group, GAG is a glycosaminoglycan residue and;
  (1) GAG is located at the 4-position, $R^3$ is located at the 3-position, $R^1$ is an OH group, $R^2$ is a COOH group and $R^3$ is an OH group when GAG is a glycosaminoglycan residue of hyaluronic acid, chondroitin, chondroitin sulfate A, C or E, dermatan sulfate, heparin or heparan sulfate excluding a reducing terminal glucuronic acid moiety or when GAG is a glycosaminoglycan residue of dermatan sulfate excluding a reducing terminal iduronic acid moiety,
  (2) GAG is located at the 4-position, $R^3$ is located at the 3-position, $R^1$ is an $OSO_3H$ group, $R^2$ is a COOH group and $R^3$ is an OH group when GAG is a glycosaminoglycan residue of chondroitin sulfate D excluding a reducing terminal glucuronic acid moiety or when GAG is a glycosaminoglycan residue of heparin or heparan sulfate excluding a reducing terminal iduronic acid moiety,
  (3) GAG is located at the 4-position, $R^3$ is located at the 3-position, $R^1$ is an OH group, $R^2$ is a COOH group and $R^3$ is an $OSO_3H$ group when GAG is a glycosaminoglycan residue of chondroitin sulfate K excluding a reducing terminal glucuronic acid moiety,
  (4) GAG is located at the 4-position, $R^3$ is located at the 3-position, at least one of $R^1$ and $R^3$ is an $OSO_3H$ group, while the other is an OH group, and $R^2$ is a COOH group when GAG is a glycosaminoglycan residue of chondroitin polysulfate excluding a reducing terminal glucuronic acid moiety,
  (5) GAG is located at the 3-position, $R^3$ is located at the 4-position, each of $R^1$ and $R^3$ is an OH group and $R^2$ is a $CH_2OH$ group when GAG is a glycosaminoglycan residue of keratan sulfate excluding a reducing terminal galactose moiety,
  (6) GAG is located at the 3-position, $R^3$ is located at the 4-position, each of $R^1$ and $R^3$ is an OH group and $R^2$ is a $CH_2OSO_3H$ group when GAG is a glycosaminoglycan residue of keratan polysulfate excluding a reducing terminal galactose moiety,
  (7) GAG is located at the 3-position, $R^3$ is located at the 4-position, $R^1$ is an $NHCOCH_3$ group, $R^2$ is a $CH_2OH$ group and $R^3$ is an OH group when GAG is a glycosaminoglycan residue of hyaluronic acid or chondroitin excluding a reducing terminal hexosamine moiety,
  (8) GAG is located at the 3-position, $R^3$ is located at the 4-position $R^1$ is an $NHCOCH_3$ group, $R^2$ is a $CH_2OH$ group and $R^3$ is an $OSO_3H$ group when GAG is a glycosaminoglycan residue of chondroitin sulfate A or K or dermatan sulfate excluding a reducing terminal hexosamine moiety,
  (9) GAG is located at the 3-position, $R^3$ is located at the 4-position, $R^1$ is an $NHCOCH_3$ group, $R^2$ is a $CH_2OSO_3H$ group and $R^3$ is an OH group when GAG is a glycosaminoglycan residue of chondroitin sulfate C or D excluding a reducing terminal hexosamine moiety,
  (10) GAG is located at the 3-position, $R^3$ is located at the 4-position, $R^1$ is an $NHCOCH_3$ group, $R^2$ is a $CH_2OSO_3H$ group and $R^3$ is an $OSO_3H$ group when GAG is a glycosaminoglycan residue of chondroitin sulfate E excluding a reducing terminal hexosamine moiety,
  (11) GAG is located at the 3-position, $R^3$ is located at the 4-position, $R^1$ is an $NHCOCH_3$ group $R^2$ is a $CH_2OH$ group and $R^3$ is an $OSO_3H$ group, or $R^2$ is a $CH_2OSO_3H$ group and $R^3$ is an OH group or an $OSO_3H$ group, when GAG is a glycosaminoglycan residue of chondroitin polysulfate excluding a reducing terminal hexosamine moiety,
  (12) GAG is located at the 4-position, $R^3$ is located at the 3-position, $R^1$ is an $NHSO_3H$ group, $R^2$ is a $CH_2OSO_3H$ group and $R^3$ is an OH group when GAG is a glycosaminoglycan residue of heparin excluding a reducing terminal hexosamine moiety,
  (13) GAG is located at the 4-position, $R^3$ is located at the 3-position, is an $NHCOCH_3$ group or an $NHSO_3H$ group, $R^2$ is a $CH_2OH$ group when $R^3$ is an $OSO_3H$ group, or $R^2$ is a $CH_2OSO_3H$ group when $R^3$ is an OH group or an $OSO_3H$ group, when GAG is a glycosaminoglycan residue of heparan sulfate excluding a reducing terminal hexosamine moiety,
  (14) GAG is located at the 4-position, $R^3$ is located at the 3-position, $R^1$ is an $NHCOCH_3$ group, $R^2$ is a $CH_2OSO_3H$ group and $R^3$ is an OH group when GAG is a glycosaminoglycan residue of keratan sulfate or keratan polysulfate excluding a reducing terminal hexosamine moiety.

5. A lipid-bound glycosaminoglycan represented by the following formula:

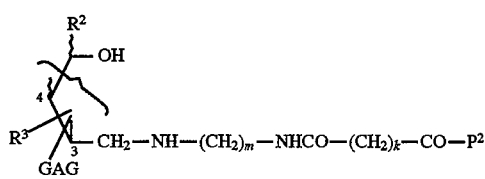
(V)

wherein $P^2$ is a lipid, GAG, $R^2$ and $R^3$ are as defined in the foregoing formula (I), m is an integer of 1 to 8 and k is an integer of 1 to 10, and;

6. A lipid-bound glycosaminoglycan represented by the following formula:

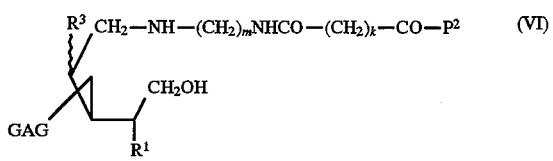
(VI)

wherein GAG, $R^1$ and $R^3$ are as defined in the forgoing formula (II), and m, k and $P^2$ are as defined in the foregoing formula (V).

7. A lipid-bound glycosaminoglycan represented by the following formula:

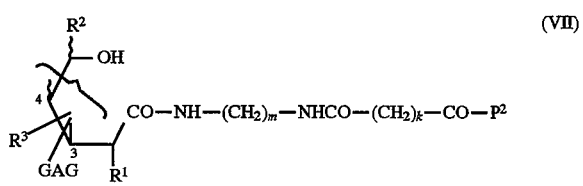
(VII)

wherein GAG, $R^1$, $R^2$ $R^3$ and are as defined in the foregoing formula (IV), and m, k and $P^2$ are as defined in the foregoing formula (V).

8. A lipid-bound glycosaminoglycan represented by the following formula:

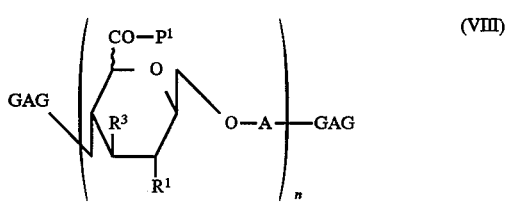
(VIII)

wherein $P^1$ is a lipid having a primary amino group, GAG is a glycosaminoglycan residue, n is an integer not more than the number of carboxyl groups contained in glycosaminoglycan, A represents hexosamine or hexosamine sulfate defined depending on the glycosaminoglycan and;

(1) each of $R^1$ and $R^3$ is an OH group when GAG is a glycosaminoglycan chain of hyaluronic acid, chondroitin, chondroitin sulfate A, C or E, or dermatan sulfate, (2) $R^1$ is an $OSO_3H$ group and $R^3$ is an OH group when GAG is a glycosaminoglycan chain of chondroitin sulfate D, (3) $R^1$ is an OH group and $R^3$ is an $OSO_3H$ group when GAG is a glycosaminoglycan chain of chondroitin sulfate K, (4) at least one of $R^1$ and $R^3$ is an $OSO_3H$ group while the other one is an OH group when GAG is a glycosaminoglycan chain of chondroitin polysulfate, and (5) $R^1$ is an OH group or an $OSO_3H$ group and $R_3$ is an OH group when GAG is a glycosaminoglycan chain of heparin or heparan sulfate.

Specific examples of the glycosaminoglycan include hyaluronic acid, chondroitin, chondroitin sulfate A, chondroitin sulfate C, chondroitin sulfate D, chondroitin sulfate E, chondroitin sulfate K, chondroitin polysulfate, dermatan sulfate (chondroitin sulfate B), heparin, heparan sulfate, keratan sulfate, and keratan polysulfate.

Preferred molecular weight of glycosaminoglycans ranges from 1,000 to 1,000,000.

In the production of the above-described lipidbound glycosaminoglycans represented by formulae (V), (VI) or (VII), a primary amino group-introduced glycosaminoglycan used as a starting material can be prepared by cleaving a reducing terminal of a glycosaminoglycan to form a lactone or an aldehyde and reacting the resulting glycosaminoglycan with alkylenediamine represented by the formula, $NH_2$—$(CH_2)_m$—$NH_2$. Alternatively, a primary amino group-introduced glycosaminoglycan can be also prepared by using amino acid having two amino groups such as lysine in place of alkylenediamine. Such alkylenediamine or amino acid can be reacted with a carboxyl group of a uronic acid moiety of a glycosaminoglycan.

The lipid having a primary amino group represented by $P^1$ in the foregoing formulae (I), (II), (III), (IV) and (VIII) is a phospholipid, such as phosphatidylethanolamine, phosphatidylserine, phosphatidylthreonine and plasmalogens, represented by the formula:

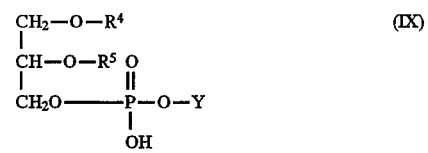
(IX)

wherein each of $R^4$ and $R^5$ is hydrogen, —CH=$CHR^6$ or —$COR^7$ (each of $R^6$ and $R^7$ is a $C_{6-24}$ alkyl group) provided that $R^4$ and $R^5$ are not hydrogen simultaneously and Y is

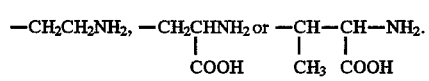

Particularly preferred are compounds in which both of $R^4$ and $R^5$ are a —$COR^7$ group such as palmitoyl (hexadecanoyl) or stearoyl (octadecanoyl) or in which $R^4$ is a —CH=$CHR^6$ group and $R^5$ is a —$COR^7$ group.

The lipid represented by $P^2$ in the foregoing formulae (V), (VI) and (VII) is a compound represented by the formula:

(X)

(XI)

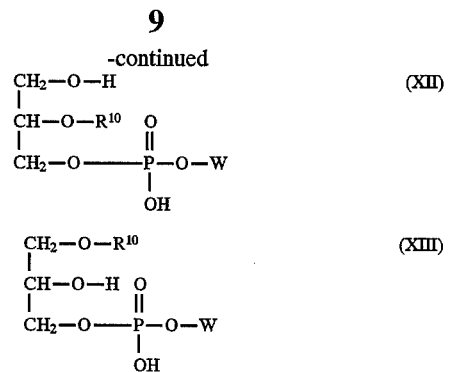

wherein $R^8$ and $R^9$ each represents hydrogen, a $C_{6-24}$ alkyl group, —CH=CHR$^6$ or —COR$^7$ wherein $R^6$ and $R^7$ are the same as above, provided that $R^8$ and $R^9$ are not hydrogen simultaneously, $R^{10}$ is a $C_{6-24}$ alkyl group, —CH=CHR$_6$ or —COR$^7$ wherein $R^6$ and $R^7$ are the same as above and W is —CH$_2$CH$_2$N$^+$(CH$_3$)$_3$ or an inositol residue. Particularly preferred are simple lipids, represented by formula (X) or (XI) in which both of $R^8$ and $R^9$ are a —COR$^7$ group such as palmitoyl (hexadecanoyl) or stearoyl (octadecanoyl) or in which $R^8$ is hydrogen and $R^9$ is a —COR$^7$ group, or a phospholipid represented by the formula (XII) or (XIII) in which $R^{10}$ is a —COR$^7$ group.

A carboxyl group-introduced lipid represented by the formula, HOOC—(CH$_2$)$_k$—CO—P$^2$, wherein P$^2$ is a lipid having a hydroxyl group, k is as defined in formula (V), used for producing a lipid-bound glycosaminoglycan represented by the foregoing formulae (V), (VI) or (VII), can be prepared by reacting a lipid having a hydroxyl group with a dicarboxylic acid represented by the formula HOOC—(CH$_2$)$_k$—COOH.

The above-described aldehyde lipid ((2)-(iv)) can be prepared by, for example, acylating or etherifying a hydroxyl group of glceraldehyde.

The processes for producing lipid-bound glycosaminoglycans of the present invention are described in detail below.

Limited oxidation of reducing terminal

In this process, the reducing terminal uronic acid, galactose or hexosamine moiety of a glycosaminoglycan is reduced and partially oxidized to cleave the reducing terminal and form an aldehyde group (a formyl group) and the thus-formed aldehyde group is subjected to a reductive alkylation reaction with a primary amino group of a lipid to give a lipid-bound glycosaminoglycan. The reaction scheme of this process is described below.

(A) In the case that glucuronic or iduronic acid in a reducing terminal is subjected to the reaction:

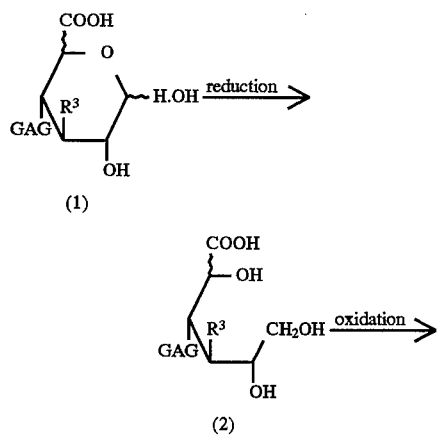

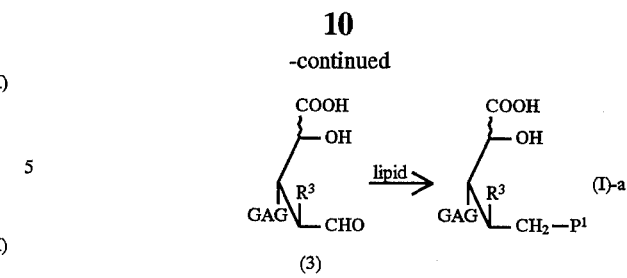

wherein $R^3$ is as defined in the foregoing formula (I) and P$^1$ is a lipid having a primary amino group.

In the case of using, as the starting material, hyaluronic acid, chondroitin, chondroitin sulfate A, chondroitin sulfate C, chondroitin sulfate E, chondroitin sulfate K, chondroitin polysulfate, dermatan sulfate, heparin or heparan sulfate, represented by the formula (1) having D-glucuronic acid or L-iduronic acid as the reducing terminal in which an OH group is linked to the 2-position carbon atom, a lipid-bound glycosaminoglycan represented by the formula (I)-a is produced in accordance with the above reaction scheme.

(B) In the case that glucosamine or galactosamine in a reducing terminal is subjected to the reaction:

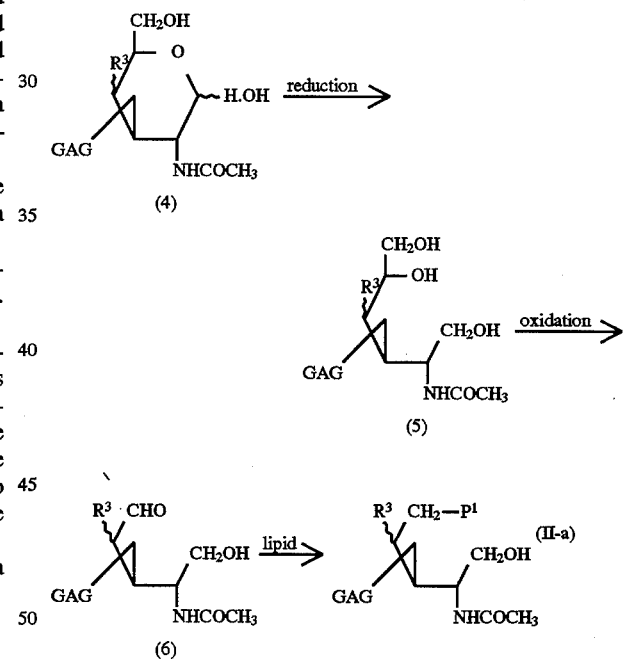

wherein $R^3$ is as defined in the foregoing formula (II) and P$^1$ is a lipid having a primary amino group.

In the case of using, as the starting material, hyaluronic acid, chondroitin, chondroitin sulfate A, chondroitin sulfate K, chondroitin polysulfate or dermatan sulfate, represented by the formula (4) having glucosamine or galactosamine as the reducing terminal in which an OH group is linked to the 6-position carbon atom, a lipid-bound glycosaminoglycan represented by the formula (II)-a is produced in accordance with the above reaction scheme.

(C) In the case that galactose in a reducing terminal is subjected to the reaction:

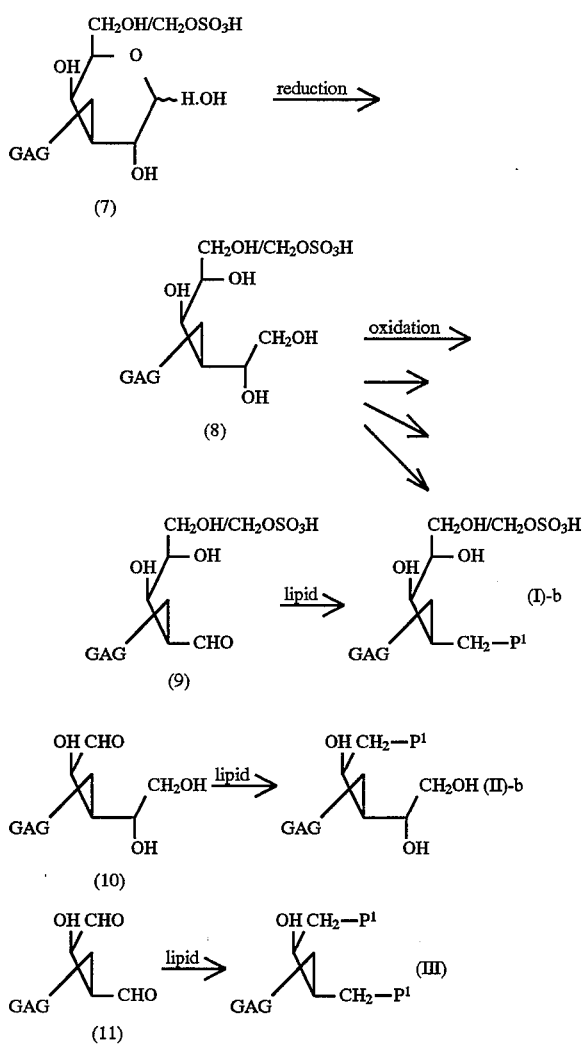

wherein $P^1$ is a lipid having a primary amino group.

In the case of using keratan sulfate and keratan polysulfate represented by the formula (7) having galactose as the reducing terminal as the starting material, a lipid-bound glycosaminoglycan represented by he formula (I)-b, (II)-b or (III) is produced in accordance with the above reaction scheme.

In the above processes (A), (B) and (C), reducing terminal sugar moieties in glycosaminoglycans represented by the formulae (1), (4) or (7) are first subjected to reduction cleavage to obtain corresponding compounds (2), (5) or (8).

Usable as a reducing agent in the reduction reaction is an alkali salt of boron hydride (borane) such as sodium borohydride, sodium cyanoborohydride or the like.

As a solvent for use in the above reduction reaction, water or a 0.05M borate buffer (pH 8.3) may be used.

The reduction reaction may be effected at a temperature of from 10° to 30° C., preferably from 15° to 25° C.

The amount of the reducing agent, though varies depending on its type, ranges from 5 to 50 equivalents, preferably from 25 to 30 equivalents, per mole of the compound (1), (4) or (7).

The thus obtained compounds of formulae (2), (5) or (8) are then subjected to partial oxidation to form aldehyde compounds represented by formulae (3), (6), (9), (10) or (11).

Usable as an oxidation agent in the oxidation reaction is an alkali salt of periodic acid such as sodium periodate, potassium periodate or the like.

The amount of the oxidation agent ranges from 1 to 10 equivalents, preferably from 3 to 6 equivalents, per mole of compounds (2), (5) or (8). The oxidation reaction may be effected at a temperature of from 0° to 10° C., preferably from 0° to 4° C.

Each of the thus-formed aldehyde compounds (3), (6), (9), (10) and (11) can be reacted with a primary amino group of a lipid in accordance with the known reductive alkylation. Thus, the lipid-bound glycosaminoglycans of the present invention represented by formulae (I), (II) or (III) are obtained.

Examples of the lipid to be used in the above reaction include phosphatidylethanolamine, phosphatidylserine, phosphatidylthreonine, ethanolamine plasmalogen, serine plasmalogen and the like.

The reductive alkylation reaction for the production of the compounds represented by formulae (I), (II) or (III) may be effected by mixing the aldehyde compound (3), (6), (9), (10) or (11) and a lipid dissolved in chloroform or the like uniformly in a solvent such as water, 0.05M phosphate buffer (pH 7.0) or dimethylformamide and allowing the mixture to react at a temperature of from 15° to 60° C. and simultaneously or thereafter carrying out a reduction reaction using a reducing agent such as sodium cyanoborohydride or the like.

Lactonization of reducing terminal

In this process, the reducing terminal uronic acid, galactose or hexosamine moiety of a glycosaminoglycan is subjected to oxidation to cleave the reducing terminal and the cleaved product is lactonized and reacted with a primary amino group of a lipid to obtain a lipid-bound glycosaminoglycan. This reaction scheme is illustrated below.

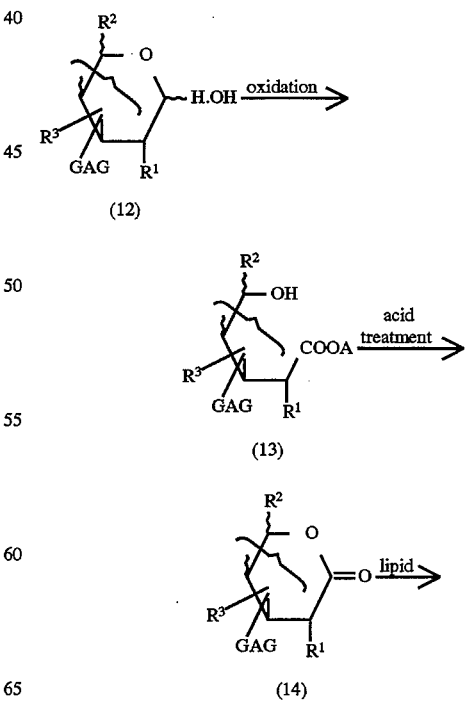

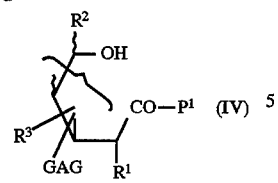

wherein each of $R^1$ $R^2$ and $R^3$ is as defined in the foregoing formula (IV), $P^1$ is a lipid having a primary amino group and A is a cation such as an alkali metal or amine.

According to this process, a glycosaminoglycan represented by formula (12) is first subjected to oxidation to cleave its reducing terminal, thereby obtaining a carboxyl compound represented by formula (13).

Usable as a starting material are compounds represented by the above formula (12) including hyaluronic acid, chondroitin, chondroitin sulfate A, chondroitin sulfate C, chondroitin sulfate D, chondroitin sulfate E, chondroitin sulfate K, chondroitin polysulfate, dermatan sulfate, heparin, heparan sulfate, keratan sulfate or keratan polysulfate.

As an oxidation agent used in the oxidation reaction, iodine, bromine or the like may be used.

The amount of the oxidation agent ranges from 2 to 20 equivalents, preferably from 5 to 15 equivalents, per mole of the compound of the formula (12).

As a solvent used in the oxidation reaction, water or a 0.05M phosphate buffer (pH 7.0) may be used.

The oxidation reaction may be effected at a temperature of from 0° to 40° C., preferably from 15° to 20° C.

The thus obtained compound of formula (13) is then subjected to acid treatment to form a lactone compound represented by formula (14).

The acid treatment is carried out using a strongly acidic cation exchange resin such as Dowex 50 (trade name, Dow Chemical Co.), Amberlite IR 120 (trade name, Rohm & Haas Co; Organo Co., Ltd.) or the like and/or acid including inorganic acid such as hydrochloric acid, sulfuric acid or the like, organic acid anhydride such as acetic anhydride, citric anhydride, succinic anhydride or the like.

The thus-formed lactone compound of formula (14) is then allowed to react with a lipid having a primary amino group to produce a lipid-bound glycosaminoglycan represented by formula (IV).

The same lipid compounds as described in the foregoing limited reducing terminal oxidation process may be used in this reaction step.

The reaction of the lactone compound of formula (14) with a lipid for the production of the compound represented by formula (IV) may be effected by dissolving the lactone compound of formula (14) in a solvent such as water, 0.05M phosphate buffer (pH 7.0) or dimethylformamide and mixing the solution with a lipid dissolved in chloroform or the like uniformly and allowing the mixture to react at a temperature of from 5° to 80° C., preferably from 30° to 60° C.

Amination of reducing terminal

In this process, each of the aldehyde compounds represented by formulae (3), (6), (9) and (10) or the lactone compound represented by formula (14) is allowed to react with an alkylenediamine compound to obtain a glycosaminoglycan derivative having a primary amino group in its reducing terminal. The thus obtained glycosaminoglycan derivative having a primary amino group is then allowed to react with a lipid derivative having a carboxyl group so that the primary amino group and the carboxyl group are linked together. Thus, a lipid-bound glycosaminoglycan is produced. The reaction scheme of this process is illustrated below:

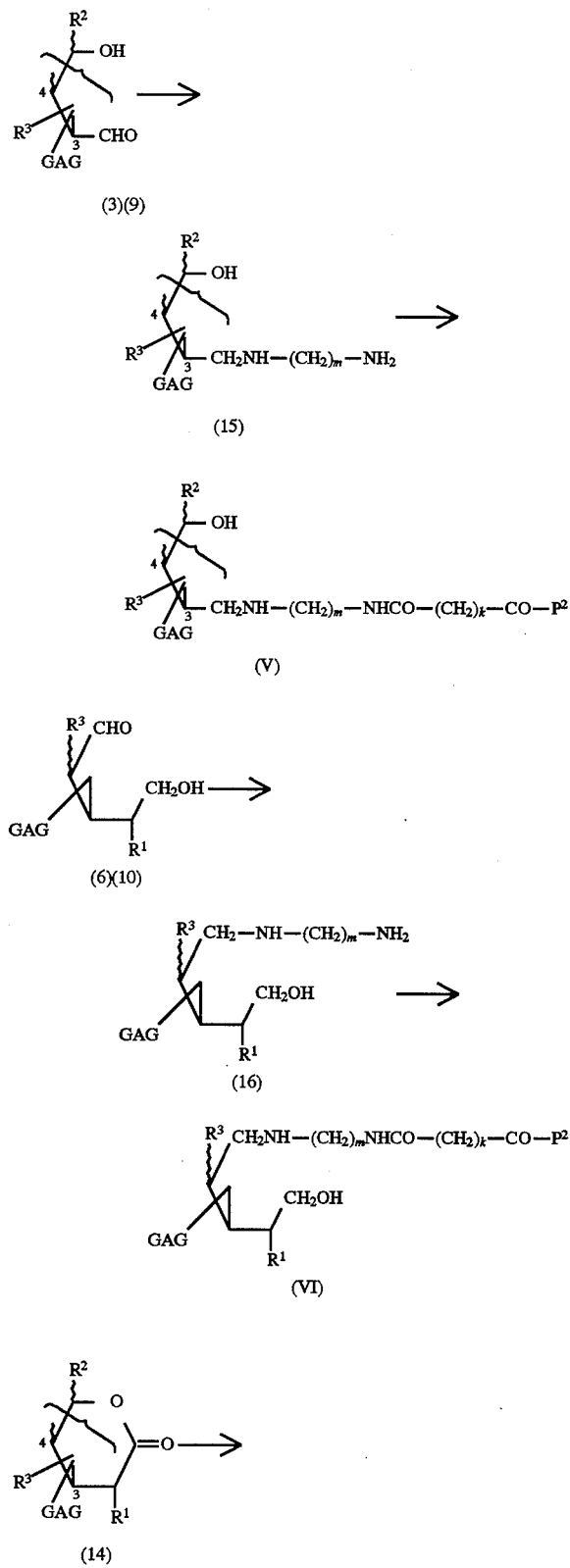

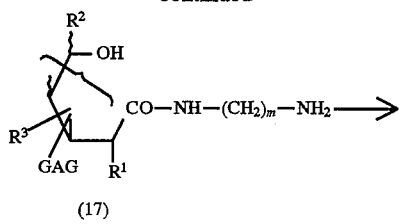

(17)

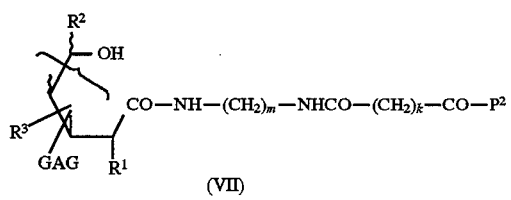

(VII)

wherein each of $R^1$, $R^2$ and $R^3$ is as defined in the foregoing formula (IV) and $P^2$ is a lipid.

A glycosaminoglycan derivative having a primary amino group in its reducing terminal, as represented by the above formula (15) or (16), is obtained by allowing each of the compounds (3), (6), (9) and (10) to react with an alkylenediamine compound in the presence of a reducing agent according to reductive alkylation reaction.

A glycosaminoglycan derivative represented by the above formula (17) is obtained by allowing compound (14) to react with an alkylenediamine compound according to the method as described above.

An alkylenediamine compound usable in this reaction may be selected from compounds represented by the following formula.

$$NH_2-(CH_2)_m-NH_2$$

wherein m is an integer of from 1 to 8.

As a reducing agent, sodium cyanoborohydride or the like may be used.

The amount of the reducing agent ranges from 10 to 100 moles per mole of the glycosaminoglycan to be used in the reaction system.

As a reaction solvent, water or a 0.05M phosphate buffer may be used.

The reaction may be effected at a temperature of from 0° to 60° C., preferably from 4° to 25° C.

A lipid derivative having a carboxyl group may be obtained by allowing a lipid compound having a hydroxyl group in its glycerol structure to react with a dicarboxylic acid or its active derivative (e.g., acid anhydride, halide).

Examples of the lipid compound to be used in this reaction include monoacylglycerol, diacylglycerol, lysophosphatidylcholine, lysophosphatidylinositol, ether lipids having a hydroxyl group, ether phospholipids having a hydroxyl group and the like.

Usable as a dicarboxylic acid or its active derivative are succinic acid, glutaric acid, adipic acid, fumaric acid, maleic acid, terephthalic acid or its acid anhydride or halide (e.g., chloride).

Usable as a condensing agent are 1-ethyl-3-(dimethylaminopropyl)carbodiimide, dicyclohexylcarbodiimide or the like.

Chloroform, acetanilide, dimethylformamide or the like may be used as the reaction solvent.

The reaction temperature may range from 0° to 60° C. when a dicarboxylic acid is used in the presence of a condensing agent, or of from 20° to 80° C. when an active derivative of dicarboxylic acid such as dicarboxylic acid anhydride is used.

Reaction of a glycosaminoglycan derivative having a primary amino group in its reducing terminal with a lipid derivative having a carboxyl group may be effected by first activating a carboxyl group in the lipid derivative in accordance with the well known means in the field of peptide chemistry and then by allowing the thus activated compound to react with the glycosaminoglycan derivative (Nobuo Izumiya, Michinori Waki et al, Pepuchido Gosei no Kiso to Jikken (Basic and Experimental Peptide Synthesis), 1985, published by Maruzen).

Activation of a carboxyl group in the lipid derivative may be effected by converting the carboxyl group into an active ester through reaction of the lipid derivative with N-hydroxysuccinimide, p-nitrophenol, N-hydroxybenzotriazole, N-hydroxypiperidine, 2,4,5-trichlorophenol or the like in the presence of a condensing agent.

Usable as a reaction solvent are chloroform, acetonitrile, dimethylformamide or the like or a mixture thereof. Usable as a condensing agent are 1-ethyl-3(dimethylaminopropyl)carbodiimide, dicyclohexylcarbodiimide or the like.

The reaction may be effected at a temperature of from 0° to 60° C.

The thus-obtained lipid derivative in which its carboxyl group has been activated is then allowed to react with the glycosaminoglycan derivative (15), (16) or (17) having a primary amino group to obtain the lipid-bound glycosaminoglycans (V), (VI) and (VII). The solvent used in this reaction is chloroform, acetonitrile, dimethylformamide or a mixture thereof. The reaction temperature ranges from 0° to 60° C.

Application of condensing agent

Each member of glycosaminoglycans, excluding keratan sulfate and keratan polysulfate, contains D-glucuronic acid or L-iduronic acid as the uronic acid moiety, and each of these acids has a carboxyl group linked to its 5-position carbon atom.

In this process, a lipid-bound glycosaminoglycan is produced by allowing the uronic acid carboxyl group to react with a primary amino group of a lipid in the presence of a condensing agent.

The reaction scheme of this process is illustrated below:

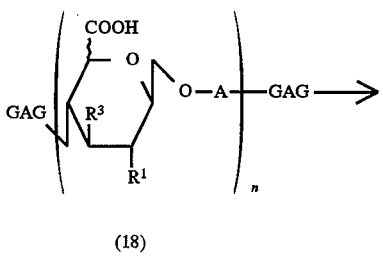

(18)

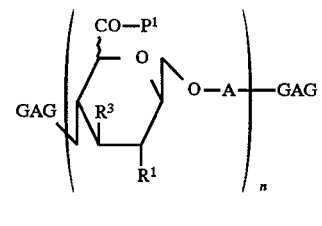

(VIII)

wherein each of $R^1$, $R^3$, A n and $P^1$ is as defined in the foregoing formula VIII).

Compounds represented by formula (18) to be used as the starting material are selected from hyaluronic acid, chondroitin, chondroitin sulfate A, chondroitin sulfate C, chondroitin sulfate D, chondroitin sulfate E, chondroitin sulfate K, chondroitin polysulfate, dermatan sulfate, heparin and heparan sulfate.

Any of the compounds described in the foregoing illustration of the limited reducing terminal oxidation process may be used as a lipid.

Examples of the condensing agent include diethylcarbodiimide, diisopropylcarbodiimide, methylpropylcarbodiimide, dicyclohexylcarbodiimide, hexamethylenecarbodiimide, heptamethylenecarbodiimide, 1-ethyl-3-(3-dimethylaminopropyl)carbodiimide, 1-cyclohexyl-3-(2-morpholinoethyl)carbodiimide-meso-p-toluenesulfonate, 1-t-butyl-3-(3-dimethylaminopropyl)carbodiimide, diphenylcarbodiimide, 4,4'-dinitrodiphenylcarbodiimide, di-p-tolylcarbodiimide, bis-(trimethylsilyl)carbodiimide or the like.

The condensing agent may be used in an amount of from 10 to 100 moles per mole of the lipid to be used.

The reaction may be effected at a temperature of from 4° to 60° C., preferably from 15° to 25° C., in a solvent such as dimethylformamide, chloroform or a mixture thereof.

Activation of glycosaminoglycan

In this process, similar to the case of the aforementioned condensing agent-applied process, the lipid-bound glycosaminoglycan (VIII) is produced by activating the uronic acid carboxyl group and then binding the activated carboxyl group to a primary amino group in a lipid.

The same glycosaminoglycan compounds and lipid compounds as described in the foregoing condensing agent-applied process may be used in this process.

Activation of a carboxyl group in the uronic acid moiety of a glycosaminoglycan compound may be effected by well known means in the field of peptide chemistry, for example by converting the carboxyl group into an activated ester through reaction of the glycosaminoglycan compound with N-hydroxysuccinimide, p-nitrophenol, N-hydroxybenzotriazole, N-hydroxypiperidine, 2,4,5-trichlorophenol or the like in the presence of a condensing agent.

The carboxyl group of the uronic acid moiety may be subjected to the reaction in the form of an amine salt such as a tri(n-butyl)amine salt or triethylamine salt; an organic base salt such as a (pyridine salt; or an alkali metal salt such as a sodium salt or potassium salt.

As a reaction solvent, dimethylformamide, pyridine, dimethylsulfoxide or the like may be used.

Usable as a condensing agent are 1-ethyl-3-(dimethylaminopropyl)carbodiimide, dicyclohexylcarbodiimide or the like.

The reaction may be effected at a temperature of from 0° to 60° C., preferably from 4° to 20° C.

By allowing the thus carboxyl group-activated glycosaminoglycan to react with a lipid, the lipid-bound glycosaminoglycan of the formula (VIII) is obtained.

This reaction may be effected by allowing the activated glycosaminoglycan to react with a lipid at a temperature of from 0° to 90° C., preferably from 25° to 60° C. in a solvent such as dimethylformamide, chloroform or a mixture thereof.

The contents of lipid portions in the lipid-bound glycosaminoglycans of the present invention represented by formulae (I) to (VIII) may range from 0.005 to 50%, preferably from 2 to 10%.

Separation and purification of the lipid-bound glycosaminoglycans obtained by the aforementioned various processes may be carried out for instance in the following manner. Final reaction solution in each procedure is mixed with ethanol which has been saturated with sodium acetate and the resulting precipitate is filtered out to remove unreacted lipid. The thus-separated precipitate is subjected to hydrophobic chromatography and the carrier is washed with an aqueous solution of a salt such as ammonium acetate, ammonium chloride, sodium chloride or the like to remove unreacted glycosaminoglycan. Thereafter, the absorbed lipid-bound glycosaminoglycan is eluted with 10 to 50% methanol solution.

The production examples of the above-described lipid-bound glycosaminoglycan are described in WO92/01720 or EP-A-493 622.

Any type of aforementioned lipid-bound glycosaminoglycan may be used as the hepatocyte spheroid-forming agent of the present invention. A lipid-bound glycosaminoglycan represented by formula (IV) is preferably used. Most preferred is a compound in which phosphatidylethanolamine covalently binds to chondroitin sulfate C whose reducing terminal has been cleaved.

Spheroids of hepatocytes may be obtained by culturing hepatocytes in the usual way using the hepatocyte spheroid-forming agent (a lipid-bound GAG) as a culture substrate which, for example, is coated on the surface of a culture dish where hepatocytes are placed.

Preferred as a culture vessel is the aforementioned positively charged polystyrene plastic dish (cf. JP-A-1-296982) such as Primaria 3801 or 3802 (trade name, Becton Dickinson & Co.). A solution containing a lipid-bound glycosaminoglycan is coated as a culture substrate on the surface of the culture dish. Coating of the lipid-bound glycosaminoglycan is carried out, for example, by adding a balanced salt solution such as Hank's solution containing the lipid-bound glycosaminoglycan in a concentration ranging from 10 µg/ml to 10 mg/ml to the culture dish and allowing it to stand at 0° C. to room temperature for 1 to 10 hours. Then, isolated hepatocytes ($1 \times 10^4$ to $1 \times 10^6$ cells/ml) are inoculated on the substrate-coated dish and cultured in a serum-free hormone-defined medium (Williams #E medium or the like) containing, for example, 10 µg of insulin, 0.1 µM $CuSO_4 \cdot 5H_2O$, 3 nM $H_2SeO_3$, 50 pM $ZnSO_4 \cdot 7H_2O$, 50 ng/ml EGF (epidermal growth factor), 50 µg/ml linoleic acid, 100 U/ml penicillin G, 100 U/ml streptomycin and 1 µg/ml fungizone, at about 37° C. under a 100% humid atmosphere of 5% $CO_2$ and 95% air. The cultivation is continued for a period of from 6 hours to several days, occasionally changing the medium with fresh ones. The hepatocytes form monolayers at the initial stage of the cultivation, and, as the cultivation progresses, the monolayers gradually aggregate to form hemispheroids of multilayer islands, and the multilayer islands further aggregate to form spherical cell clusters which subsequently separate from the surface of the dish to form floating spheroids in the liquid medium. Each of the thus formed spheroids may have a diameter of from 50 to 150 µm, preferably from 70 to 120 µm, and may be composed of a total of 50 to 300 cells, preferably 70 to 250 cells.

The floating spheroids can be recovered from the culture by centrifuging the culture at 50×G for 1 minute, removing the supernatant with suction and collecting the residue.

It is considered that spheroid formation occurs because adhesion of hepatocytes to the culture substrate is inhibited in the presence of a lipid-bound glycosaminoglycan, and the spheroid-forming activity has a mutual relation to the adhesion inhibition activity of the lipid-bound glycosaminoglycan which inhibits adhesion of baby hamster kidney cells (BHK cells) and the like to a fibronectin substrate.

The spheroid formation can be effected at a low concentration of a lipid-bound glycosaminoglycan which has a high adhesion inhibition activity. Preferably, such a lipid-bound glycosaminoglycan may have a cell adhesion inhibition activity of 400 µg/ml or below as a 50% inhibition concentration ($IC_{50}$) when measured in accordance with a procedure described in the following Examples.

The spheroid cannot be formed using glycosaminoglycan alone. It is a completely unexpected finding that the spheroid formation can be effected using a lipid-bound glycosaminoglycan as a culture substrate within a markedly shorter period of time in comparison with the case of using a positively charged polystyrene plastic dish alone or of the known proteoglycans. Such a finding enabled practical culture of hepatocytes.

It was confirmed that the spheroids of hepatocytes thus obtained could secrete albumin at a high level and maintain liver-specific differentiation functions. In addition, growth of cells in these spheroids was found to be suppressed because $^3$H-thymidine incorporation was hardly observed, which indicated that the spheroid formation was different from a cancer-like proliferation.

Thus, according to the present invention, floatable spheroids of hepatocytes which maintain liver-specific functions and spheroid bodies for a prolonged period of time can be efficiently obtained. Since, unlike proteoglycans, a lipid-bound glycosaminoglycan of the present invention (which is considered to function as an artificial extracellular matrix) can be easily synthesized, it is useful for the development of an artificial liver function-aiding device.

The following examples are provided to further illustrate the present invention. It is to be understood, however, that the examples are for purpose of illustration only and are not to be construed to limit the scope of the invention.

REFERENCE EXAMPLE

Preparation of phospholipid-bound glycosaminoglycan by lactonization of reducing terminal (1) Preparation of reducing terminal-oxidized glycosaminoglycan 1) Preparation of reducing terminal-oxidized hyaluronic acid 500 mg of hyaluronic acid (HA1 ; MW, 10,000; cockscomb origin) was dissolved in 10 ml of water, and the solution was mixed with 5 ml methanol solution of 0.1M iodine and incubated at room temperature for 6 hours to effect the reaction. To the resulting reaction mixture was added about 5 ml of 0.1N potassium hydroxide to decolor free iodine. Potassium acetate-saturated ethanol was added to the resulting solution to form a precipitate and the precipitated product was collected by filtration, washed thoroughly with ethanol and then dried under a reduced pressure. Thus, 423 mg of potassium salt of reducing terminal-oxidized hyaluronic acid (lot No. 400) was obtained. Reducing sugar was not detected in the product when checked by Somogyi-Nelson method.

2) Preparation of reducing terminal-lactonized hyaluronic acid 400 mg of the lot No. 400 reducing terminal-oxidized hyaluronic acid was dissolved in 10 ml of water, and the solution was passed through 50 ml of a column of a strongly acidic ion exchange resin (Dowex 50($H^+$)) for 1 hour. Thus, a solution containing 390 mg of reducing terminal-lactonized hyaluronic acid was obtained. Reducing sugar was not detected in the solution when checked by Somogyi-Nelson method.

The thus-obtained solution was neutralized with tri-n-butylamine and subsequently lyophilized to obtain 400 mg of tri-n-butylamine salt of reducing terminal-lactonized hyaluronic acid (lot No. 500).

3) Preparation of other reducing terminal-lactonized glycosaminoglycans

Reducing terminal-oxidized glycosaminoglycans were prepared according to the above procedure 1) under conditions shown in Table 1, using each of the following starting materials: chondroitin (CH; MW, 15,000), chondroitin sulfate C (CS (S1); MW, 10,000: CS (S3); MW, 30,000: and CS (S6); MW, 60,000), dermatan sulfate (DS; MW, 15,000), heparin (Hep; MW, 15,000) and heparan sulfate (HS; MW, 15,000). The thus obtained samples were subjected to the above procedure 2) under conditions shown in Table 2 to produce reducing terminal-lactonized glycosaminoglycans.

TABLE 1

| Lot No. | Product | Reaction condition GAG/0.1M $I_2$/0.1N KOH (mg/ml/ml) | Yield (mg) | Somogyi-Nelson |
|---|---|---|---|---|
| 401 | CH-COOK | 1000/13.4/13.4 | 828 | — |
| 402 | CS(S1)-COOK | 1000/19.8/19.8 | 901 | — |
| 402-2 | CS(S3)-COOK | 1000/3.3/3.3 | 895 | — |
| 402-3 | CS(S6)-COOK | 1000/4.95/4.95 | 913 | — |
| 404 | DS-COOK | 100/0.67/0.67 | 91 | — |
| 405 | Hep-COOK | 1000/6.7/6.7 | 902 | — |
| 406 | HS-COOK | 100/1.34/1.34 | 88 | — |

*Somogyi-Nelson: presence (+) or absence (−) of reducing sugar determined by Somogyi-Nelson method.

TABLE 2

| Lot No. | Product | Reaction condition GAG-COOK/Dowex 50 ($H^+$) (mg/ml) | Yield (mg) | Somogyi-Nelson |
|---|---|---|---|---|
| 501 | CH-lactone | 800/400 | 780 | — |
| 502 | CS(S1)-lactone | 900/450 | 805 | — |
| 502-2 | CS(S3)-lactone | 800/400 | 850 | — |
| 502-3 | CS(S6)-lactone | 900/450 | 887 | — |
| 504 | DS-lactone | 90/100 | 96 | — |
| 505 | Hep-lactone | 900/400 | 946 | — |
| 506 | HS-lactone | 80/40 | 72 | — |

*Somogyi-Nelson: presence (+) or absence (−) of reducing sugar determined by Somogyi-Nelson method.

(2) Preparation of L-(α-phosphatidyl)ethanolamine dipalmitoyl (PPEADP)-bound glycosaminoglycan 1) Preparation of L-(α-phosphatidyl)ethanolamine dipalmitoyl-bound hyaluronic acid

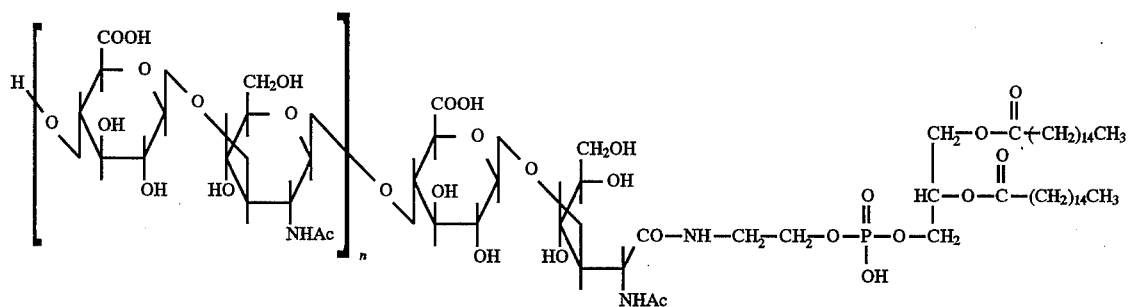

and

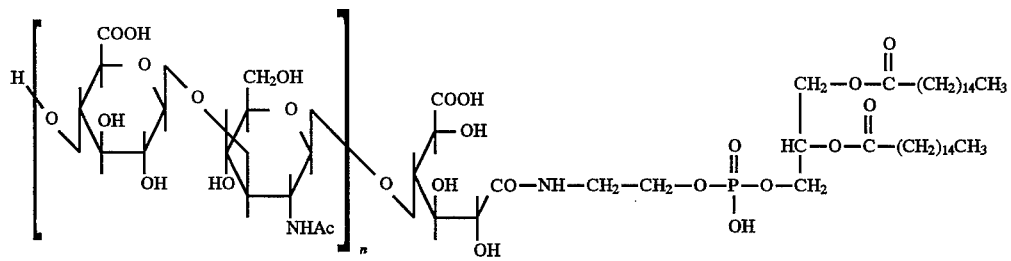

n: average 25

400 mg of lot No. 500 reducing terminal-lactonized hyaluronic acid was dissolved in 200 ml of dimethylformamide and 27.6 mg of PPEADP dissolved in chloroform was added thereto. The resulting mixture was allowed to react at 70° C. for 2 hours. After removing chloroform from the reaction mixture by distillation, excess volume of sodium acetate aqueous solution was added to the residue to make the reaction product into sodium salt. Sodium acetate-saturated ethanol was added thereto to form a precipitate and the thus-formed precipitate was collected by filtration. The precipitate was dissolved in 0.3M ammonium acetate solution and applied to a hydrophobic chromatographic column (400 ml of TSK gel Phenyl Toyopearl 650M, Tosoh Corporation) for adsorption. The column was washed thoroughly with 0.3M ammonium chloride solution and then elution was carried out with 30% methanol aqueous solution. The reaction product of interest was found in the 30% methanol-eluted fraction, while unreacted hyaluronic acid was found in the unadsorbed fraction and washings. The 30% methanol-eluted fraction was concentrated under a reduced pressure, desalted by dialysis, and then lyophilized to obtain 36 mg of the desired product (lot No. 600).

Phosphorus content: 0.30%
PPEADP content: 6.44%
Hyaluronic acid content: 82.37%

(2) Preparation of other L-(α-phosphatidyl)ethanolamine dipalmitoyl-bound glycosaminoglycans PPEADP-bound glycosaminoglycans shown in Table 3 were prepared from the reducing terminal-lactonized glycosaminoglycans shown in Table 2, and PPEADP in accordance with the above procedure (1)-2) under conditions shown in Table 3. Results of the analysis

TABLE 3

| Lot No. | Product | Reaction condition GAG-lactone/PPEADP (mg/mg) |
|---|---|---|
| 601 | CH-PPEADP | 700/32.3 |
| 602 | CS(S1)-PPEADP | 800/55.4 |

TABLE 3-continued

| Lot No. | Product | Reaction condition GAG-lactone/PPEADP (mg/mg) |
|---|---|---|
| 602-2 | CS(S3)-PPEADP | 400/9.26 |
| 602-3 | CS(S6)-PPEADP | 800/9.00 |
| 604 | DS-PPEADP | 90/4.15 |
| 605 | Hep-PPEADP | 800/36.91 |
| 606 | HS-PPEADP | 70/3.31 |

TABLE 4

| Lot No. | Yield (mg) | PPEADP (%) | GAG (%) |
|---|---|---|---|
| 601 | 70.2 | 4.30 | 90.90 |
| 602 | 88.0 | 6.41 | 85.17 |
| 602-2 | 20 | 2.01 | 89.70 |
| 602-3 | 56.2 | 1.08 | 92.00 |
| 604 | 4.5 | 4.00 | 90.66 |
| 605 | 24 | 4.11 | 90.01 |
| 606 | 5.74 | 4.22 | 88.21 |

EXAMPLE 1

(1) Coating of phospholipid-bound glycosaminoglycans to culture dishes

Each of five different types of phospholipid-bound glycosaminoglycans shown in Table 5 was dissolved in Hanks' solution (Proc. Soc. Exp. Biol. Med., 71, 196 (1949) ) to various final concentrations ranging from 1 to 100 µg/ml, and a 2 ml portion of each of the resulting solutions was poured into a polystyrene plastic dish (Primaria 3802, 60 mm in diameter, available from Becton Dickinson & Co.) and the dish was allowed to stand about 10 hours at 4° C. to coat the phospholipid-bound glycosaminoglycan.

(2) Isolation and cultivation of adult rat hepatocytes

Primary culture of adult rat hepatocytes was conducted in accordance with the method of Seglen et al (In Methods in Cell Biology, D.M. Prescott, Ed., Vol. XIII, pp. 29–83

(1976) Academic Press, New York) to obtain cultured hepatocytes. Each of Sprague-Dawley rats (seven weeks old, weighing 150 to 200 g) was anesthetized by intraperitoneal injection of 10 mg (200 μl portion of 50 mg/ml solution) of Nembutal (trade name, Abbot Labs; pentobarbiturate). Each of the thus-anesthetized rat was subjected to laparotomy to insert a catheter-linked tube into the portal vein and to pass a pre-perfusion solution into the vein at a flow rate of 30 ml/min. After ligation of the inferior vena cava, the pre-perfusion was carried out for 2 to 3 minutes through the tube from the superior vena cava. After the pre-perfusion was completed, the pre-perfusion solution was replaced with a 0.05% collagenase perfusion solution kept at 37° C., and the collagenase perfusion was carried out for 7 to 10 minutes. Thereafter, the liver was excised, put in a vessel containing a cold cell washing solution (Hanks' solution) and, while cooling on an ice bath, loosened into fine slices using a knife to recover cells.

The thus obtained cell suspension was centrifuged for 1 minute at 50×G and the resulting supernatant was removed by careful suction. The cells remained in the form of pellet in the centrifugation tube were suspended in the Williams #E medium and centrifuged for 1 minute at 50×G. By repeating the latter centrifugation step twice, hepatocytes were separated from non-parenchymal cells (endothelial cells, Kupffer cells and fat storing cells (Ito cells)).

After counting the number of cells and measuring viability (by dye-exclusion test using 0.6% trypan blue), the thus-isolated hepatocytes were diluted to a density of $3 \times 10^5$ cells/ml with Enat's HDM medium modified by Koide et al (Shinji, T., Koide, N. and Tsuji, T., Cell Struct. Funct. 13, 179–188 (1988))) (Williams #E medium containing 10 μg of insulin, 0.1 μM $CuSO_4 \cdot 5H_2O$, 3 nM $H_2SeO_3$, 50 pM $ZnSO_4 \cdot 7H_2O$, 50 ng/ml EGF (epidermal growth factor, Takara Shuzo Co., Ltd.), 50 μg/ml linoleic acid, 100 U/ml penicillin G, 100 U/ml streptomycin and 1 μg/ml fungizone). The PPEADP-bound glycosaminoglycan-coated polystyrene plastic dish (Falcon 3802, 60 mm in diameter) as prepared in (1) was washed twice with the Hanks' solution and inoculated with a 4 ml portion of the thus-prepared cell suspension. The cells were cultured at 37° C. under a 100% humid atmosphere of 5% $CO_2$ and 95% air. Half the volume of the medium was replaced with fresh medium after 6 hours, 1 day and 3 days of the cultivation. Microscopic observations and photography were carried out in the first day and second day.

(3) Results

Significant enhancement of the formation of spheroids was observed in a dish coated with 10 μg/ml concentration of CS(S3)-PPEADP (Lot No. 602-2; to be referred to as "CS-PPEDAP" hereinafter). With the concentration of 10 μg/ml, multilayer island-like hemispheroids were observed after 1 day of the cultivation, and most of them became floating spheroids 2 days after the cultivation. The spheroid formation was not observed when a dish coated with CS(S3) alone or PPEADP alone was used, and the effect of CS-PPEADP did not increase when its concentration was increased to 100 μg/ml. In a control dish (not coated), additional 2 to 3 days were required to form spheroids, and only a few completely floating spheroids were observed. Results of the spheroid formation in dishes coated with various PPEADP-bound glycosaminoglycans are shown in Table 5.

TABLE 5

| Lot No. (10 μg/ml) | Degree of spheroid formation |
| --- | --- |
| 602-2 | +++ |
| 604 | + |
| 606 | + |
| 600 | + |
| 601 | + |
| Control (untreated dish) | + |

Note:
+++: very good, ++: good, +: control level, –: inhibited

Culture dishes which had been coated with fibronectin in advance were further coated with each of the compounds of Table 5, in order to examine as to whether these compounds inhibit adhesion of baby hamster kidney cells (BHK 21 cells) to fibronectin substrate.

FIG. 2 shows concentration curves which indicate adhesion inhibition effects of various PPEADP-bound glycosaminoglycans. As shown in the figure, CS-PPEADP showed the highest inhibition activity, followed by DS-PPEADP, HS-PPEADP, HA-PPEADP and CH-PPEADP in that order. The $IC_{50}$ values calculated from these curves are shown in Table 6.

TABLE 6

| Lot No. | $IC_{50}$ for adhesion inhibition (μg/ml) |
| --- | --- |
| 602-2 | 0.77 |
| 604 | 1.49 |
| 606 | 4.9 |
| 600 | 17.2 |
| 601 | 80.8 |

The above results suggest that the hepatocyte spheroid-forming activity of the agents of the present invention is correlated to their adhesion inhibition activity against fibronectin substrate.

EXAMPLE 2

Spheroids formed using CS-PPEADP, a positively charged plastic dish or collagen as culture substrates were examined for the liver-specific function and proliferation.

(1) Primary culture of adult rat hepatocytes

Hepatocytes were isolated in the same manner as described in Example 1 and adjusted to a density of $3 \times 10^5$ cells/mi.

(2) Coating of culture substrate

A 1 ml portion of Hanks' solutions containing 10 μg/ml of CS-PPEADP was poured into a polystyrene plastic dish (Primaria 3801, 35 mm in diameter, Becton Dickinson & Co.), and a 1 ml portion of 0.02N acetic acid solution containing 0.03% collagen (Cell Matrix IC, Koken Co., Ltd.) into a polystyrene plastic dish (Falcon 3001, 35 mm in diameter, Becton Dickinson & Co.). Each of the resulting dishes was allowed to stand for about 10 hours at 4° C. to coat the culture substrate. The thus-coated dishes were washed twice with the Williams medium.

(3) Measurement of proliferation potency—measurement of DNA replication activity using $^3H$-thymidine—

The isolated hepatocytes as mentioned in (1) above were inoculated in the dishes prepared in (2) above in an inoculum size of 1.5 ml suspension per dish and were cultured in the same manner as in Example 1. The medium was replaced with fresh medium 24 hours before the labeling experiment.

After 24 hours, 1 μCi (3.7×10⁴ Bq) of ³H-thymidine was added to the medium and the cells were further cultured at 37° C. for 24 hours. After cultivation in the presence of ³H-thymidine, the medium was removed and the cells were washed with ice-cold phosphate-buffered saline (PBS). Thereafter, 1 ml of cooled 10% Trichloroacetic acid (TCA) was added to the washed cells to fix them. After 1 hour of storage in a refrigerator, TCA was removed by suction, and the resulting cells were mixed with 1 ml of 1N NaOH solution, and incubated at 37° C. for 1 hour to lyse the hepatocytes completely. A 100 μl portion of the thus-obtained cell lysate was spared for use in the DNA measurement, and the rest was transferred into a small test tube. A 0.3 ml portion of 100% TCA was added to the lysate-containing test tube, and the mixture was ice-cooled for 10 minutes and then subjected to centrifugation at 10,000 rpm for 20 minutes. After removing the supernatant, the resulting precipitate was mixed with 0.5 ml of 10% TCA, and the mixture was heated for 15 minutes in a boiling bath, cooled down and then centrifuged at 10,000 rpm for 20 minutes. A 0.3 ml portion of the resulting supernatant was put in a scintillation vial and mixed with 3 ml of a scintillator to measure radioactivity of tritium (3H) using a liquid scintillation counter.

(4) Measurement of albumin secretion as an index of liver-specific functions

The amount of secreted albumin was measured by enzyme immunoassay (EIA) utilizing a sandwich technique making use of polystyrene beads.

Anti-rat albumin antibody IgG fraction (available from Cappel) was diluted with a 0.1M Tris-HCl buffer/0.15 M NaCl solution to a final concentration of 10 μg/ml. To 1 ml portion of the thus-prepared antibody solution was added four polystyrene beads (¼φ, Pierce), followed by 2 hours of degassing with gentle stirring at room temperature. After overnight standing at 4° C., the resulting beads were washed three times with PBS and added to a solution consisting of 50 mM phosphate buffer (pH 7.4), 0.15M NaCl, 0.1% gelatin and 0.02% sodium azide. The thus-prepared anti-rat albumin antibody-bound beads were stored at 4° C. (preservable for 2 to 3 months).

A 100 μl portion of three samples (a 5 μl portion of the 1.5 ml culture supernatant of hepatocyte culture incubated under certain conditions for 24 hours was diluted with the above-mentioned phosphate buffer) or a standard rat albumin solution was mixed with 500 μl of the above-mentioned phosphate buffer. After adding one anti-rat albumin antibody-bound bead, the thus-prepared mixture was incubated at room temperature for 4 hours with stirring. The bead was washed three times with a PBS/0.05% Tween 20 solution (5 minutes each) and added to 500 μl of a solution of a peroxidase-labeled anti-rat albumin antibody IgG (available from Cappel) which had been diluted with 0.1% gelatin-containing PBS/0.05% Tween 20 solution by a factor of 1×10⁴. After overnight incubation at 4° C. with gentle stirring, the thus-treated bead was washed three times with the PBS/0.05% Tween 20 solution (5 minutes each), washed once with PBS for 5 minutes, and then added to 1 ml of a chromogenic reagent solution which had been prepared by dissolving 50 mg of o-phenylenediamine and 10 μl of 30% $H_2O_2$ in 100 ml of 0.1M Tris-HCl buffer (pH 7.4). After 30-minute incubation at room temperature with gentle stirring, the reaction was terminated by adding 1 ml of 1.3N sulfuric acid. The developed color was measured based on the absorbance at 492 nm.

(5) Quantitative determination of DNA

A 80 μl portion of each sample dissolved in 1N NaOH solution was neutralized with acetic acid and subjected to ethanol precipitation. The resulting precipitate was dissolved in 100 μl of 1N $NH_4OH$ solution and then dried under a reduced pressure. To the thus-dried sample was added 100 μl of diaminobenzoic acid (DABA) reagent solution (0.4 g of DABA.2HCl dissolved in 1 ml of distilled water; 10 to 20 mg of Norit A (trade name, charcoal, activated acid washed with HCl, powder, Nacalai Tesque) was used as a decoloring agent when the solution showed a dark brown color), followed by thorough stirring. The thus-prepared sample was sealed with parafilm and incubated for 30 minutes in a 60° C. water bath. After cooling, the thus-treated sample was mixed thoroughly with 2 ml of 0.6N $HClO_4$, and the mixture was centrifuged at 10,000 rpm for 5 minutes. Then, absorbances of the resulting supernatant were measured at an excitation wave length of 415 nm and at an emission wave length of 515 nm using a fluorophotometer.

(6) Results

In the CS-PPEDAP-coated dish, the cells started to assemble after 1 day of the cultivation and most of them formed floating spheroids in the second day. The assembled cells after 1 day of the cultivation seemed to simply adhere one another in view of the rough surface of the assembled layer. From the second day, organization of spheroids progressed and their surfaces became smooth. In the positively charged plastic dish which had not been coated, the spheroid formation started a half day to one day later than the case of the CS-PPEADP-coated dish. Multilayer island-like hemispheroids started to float gradually, but requiring nearly one more day of delay to complete their floating. In the dish coated with collagen, the cells started to adhere and spread about 6 hours after the cultivation and formed fine monolayers after 1 day of the cultivation. As the cultivation progressed, the cells continued to proliferate and the cell density increased, but the cell layers started to shrink in the fourth day and were peeled off clearly from the periphery in the dish in the fifth day to form a small floating membrane.

Incorporation of ³H-thymidine measured during the culturing period is shown in Table 7.

TABLE 7

| Day | CS-PPEADP (dpm) | Uncoated (dpm) | Collagen (dpm) |
| --- | --- | --- | --- |
| 1 | 9037 ± 943 | 11543 ± 1444 | 13178 ± 1054 |
| 2 | 161106 ± 8966 | 224253 ± 39158 | 424915 ± 25774 |
| 3 | 190661 ± 11062 | 233336 ± 18039 | 564520 ± 37481 |
| 4 | 91490 ± 10449 | 80030 ± 6075 | 319286 ± 184 |
| 5 | 41456 ± 2268 | 46194 ± 5832 | 28958 ± 519 |

It can be seen from the above table that proliferation of the cells is suppressed most strongly in the case of using the CS-PPEDAP-coated dish, followed by the uncoated dish and the collagen-coated dish in that order. In the case of the collagen-coated dish, incorporation of ³H-thymidine decreased sharply on the fifth day, which seems to be the result of an increase in cell density due to shrinkage of monolayers and subsequent formation of a three-dimensional structure.

With respect to the measurement of secreted albumin as an index of liver-specific functions, 20 to 1,000 ng/ml of rat albumin could be quantitatively determined under the set conditions. Results of the measurement of the amount of albumin secreted in 24 hours per DNA under each culture condition are shown in FIG. 3. When CS-PPEADP was used as the culture substrate, formation of spheroids was observed in the early stage of the cultivation, and a tendency to maintain the liver function was significantly superior to that observed in the case of using the uncoated positively charged plastic dish. Taking account of the results of the $^3$H-thymidine incorporation shown in Table 7 and the observation of cell morphology, the early stage formation of spheroids seemed to be the main cause of such a liver function maintaining tendency. When collagen was used as the culture substrate, the liver-specific function decreased at the early stage of the cultivation.

Thus, it is suggested that hepatocyte spheroids formed by using the spheroid-forming agent of the present invention can maintain good liver-specific functions of hepatocytes.

While the invention has been described in detail and with reference to specific embodiments thereof, it will be apparent to one skilled in the art that various changes and modifications can be made therein without departing from the spirit and scope thereof.

What is claimed is:

1. A process for forming spheroids of hepatocytes which comprises culturing hepatocytes with a lipid-bound glycosaminoglycan as a culture substrate, wherein said lipid-bound glycosaminoglycan is phosphatidyl ethanolamine diacyl bound chondroitin sulfate.

2. A process for forming spheroids of hepatocytes which comprises culturing hepatocytes with a lipid-bound glycosaminoglycan as a culture substrate, wherein said lipid-bound glycosaminoglycan is phosphatidyl ethanolamine dipalmitoyl bound chondroitin sulfate.

3. A process for forming spheroids of hepatocytes which comprises culturing hepatocytes with a lipid-bound glycosaminoglycan as a culture substrate, wherein said lipid-bound glycosaminoglycan has an $IC_{50}$ for cell adhesion inhibition activity of 1.49 μg/ml or less.

* * * * *